US012648918B2

(12) United States Patent
Gaillard et al.

(10) Patent No.: US 12,648,918 B2
(45) Date of Patent: Jun. 9, 2026

(54) USE OF PARABULIN FOR TARGETING PROTOZOAN TUBULIN FOR THE INHIBITION OF PROTOZOAN REPLICATION

(71) Applicant: Paul Scherrer Institut, Villigen PSI (CH)

(72) Inventors: Natacha Gaillard, Endingen (CH); Ashwani Sharma, Brugg (CH); Michel Steinmetz, Basel (CH)

(73) Assignee: Paul Scherrer Institut, Villigen PSI (CH)

( * ) Notice: Subject to any disclaimer, the term of this patent is extended or adjusted under 35 U.S.C. 154(b) by 552 days.

(21) Appl. No.: 18/248,097

(22) PCT Filed: Sep. 21, 2021

(86) PCT No.: PCT/EP2021/075957

§ 371 (c)(1),
(2) Date: Apr. 6, 2023

(87) PCT Pub. No.: WO2022/073759

PCT Pub. Date: Apr. 14, 2022

(65) Prior Publication Data

US 2023/0364041 A1 Nov. 16, 2023

(30) Foreign Application Priority Data

Oct. 6, 2020 (EP) .................................... 20200188

(51) Int. Cl.
*A61P 33/02* (2006.01)
*A61K 31/165* (2006.01)

(52) U.S. Cl.
CPC ............ *A61K 31/165* (2013.01); *A61P 33/02* (2018.01)

(58) Field of Classification Search
CPC .............................. A61K 31/165; A61P 33/02
See application file for complete search history.

(56) References Cited

PUBLICATIONS

Desta et. al. (Med. Chem. Res. (2011) 20:364-369). (Year: 2011).*
Desta Dereje et al: "Synthesis and antiprotozoal activity of 1,2,3,4-tetrahydro-2-thioxopyrimidine analogs of combretastatin A-4", Medicinal Chemistry Research, vol. 20, No. 3, Mar. 9, 2010 (Mar. 9, 2010), pp. 364-369, XP055783937, ISSN: 1054-2523, DOI: 10.1007/s00044-010-9334-1 Retrieved from the Internet: URL:http://link.springer.com/article/10.1007/s00044-010-9334-1/fulltext.html.
Gaillard Natacha et al: "Inhibiting parasite proliferation using a rationally designed anti-tubulin agent", EMBO Molecular Medicine, vol. 13, No. 11, Oct. 18, 2021 (Oct. 18, 2021), XP055873700, ISSN: 1757-4676, DOI: 10.15252/emmm.202013818, Retrieved from the Internet: URL:https://onlinelibrary.wiley.com/doi/fullxml/10.15252/emmm.202013818>.

* cited by examiner

*Primary Examiner* — Marcos L Sznaidman
(74) *Attorney, Agent, or Firm* — Laurence A. Greenberg; Werner H. Stemer; Ralph E. Locher

(57) ABSTRACT

A determination has been made that apicomplexan tubulin, an essential parasite component, is an excellent drug target. Here, it is shown that it is possible to specifically target parasite tubulins, without harming the mammalian host. A compound has been identified that destabilizes specifically parasite MTs and inhibits essential parasite processes of replication and host cell invasion. This provides a new strategy to tackle the issue of drug resistance development. Specifically, the use of the compound parabulin and/or its derivates in the process of targeting protozoan tubulin for the inhibition of the replication of protozoans in mammalian organism, wherein parabulin has the following molecular weight, sum formula, name and structure:

MW: 373.4 Da;

Formula: $C_{20}H_{23}NO_6$, •Name (s): 3-(3,4-dimethoxyphenyl)-N-[(3,4,5-trimethoxyphenyl)methyl]prop-2-enamide; (2E)-3-(3,4-Dimethoxyphenyl)-N-(3,4,5-trimethoxyphenyl)acrylamid;

SMILES:

0(C1=C(OC)C=CC(=C1)C=CC(=0)N(CC2=CC(=C(OC)C(=C2)OC)OC)[H])C.

1 Claim, 4 Drawing Sheets

FIG. 4A
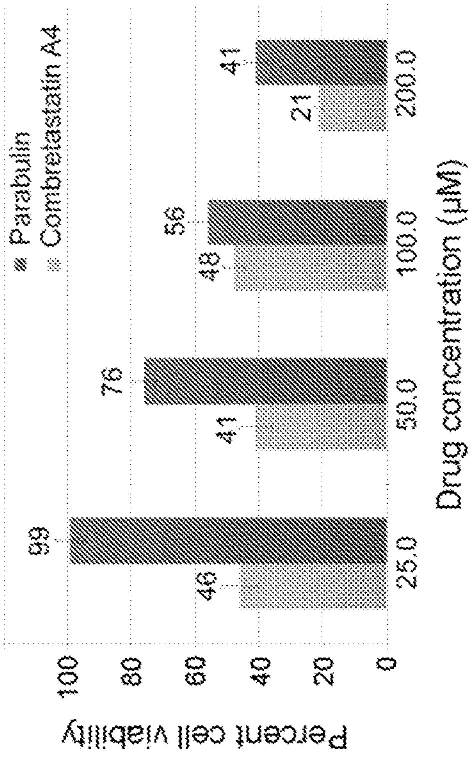
FIG. 4B
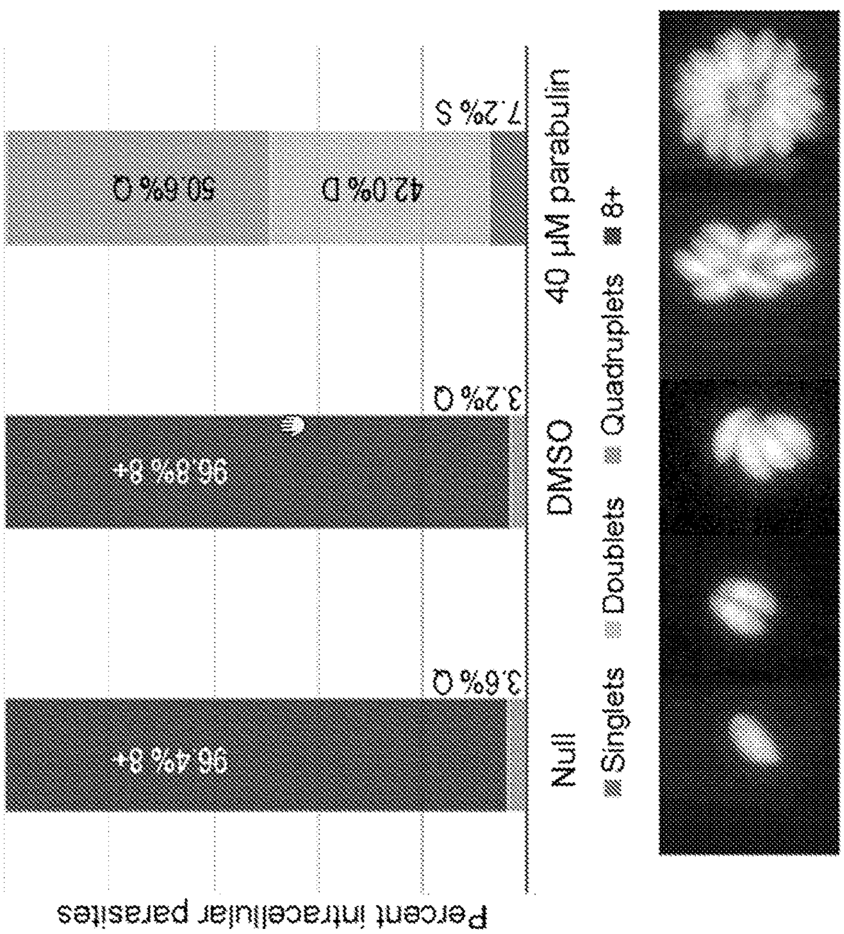
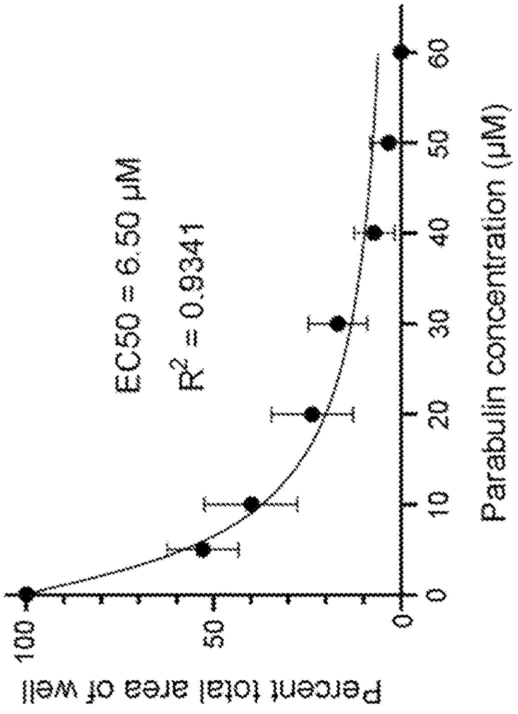
FIG. 4C

USE OF PARABULIN FOR TARGETING PROTOZOAN TUBULIN FOR THE INHIBITION OF PROTOZOAN REPLICATION

FIELD AND BACKGROUND OF THE INVENTION

The present invention relates to the use of the chemical compound parabulin the process of targeting protozoan tubulin.

Successful parasitism relies mainly on the parasites' ability to rapidly invade host cells, to evade the host immune response and to robust intracellular growth. The parasite microtubule (MT) cytoskeleton plays a central role in the process of parasite replication and it constitutes as well a key component of the parasite invasion machinery. MTs are dynamic protein filaments made up of polymerized αβ-tubulin heterodimers that undergo phases of growth and shrinkage, a property called dynamic instability. Microtubule-targeting agents (MTAs) are among the most important medical weapons available to combat cancer. They act by either stabilizing MTs (microtubule stabilizing agents, MSAs) or destabilizing MTs (microtubule destabilizing agents, MDAs).

Recent major advances in the structural characterization of tubulin-MTA complexes has led to the identification of six distinct drug-binding sites on mammalian tubulin. Although the tubulin sequence is highly conserved among eukaryotes, protozoan tubulins are much less sensitive to well-known MTAs like, for example, colchicine. Similarly, dinitroaniline family of drugs are effective towards plant and parasite tubulins but not against mammalian tubulins. These observations highlight subtle structural differences in the drug-binding sites of protozoan compared to human tubulins, which could be exploited for the development of novel parasite-specific anti-tubulin drugs. Additionally, by choosing an essential protein like tubulin that contains multiple drug-binding sites, combination therapies that target distinct pockets at the same time could represent a unique strategy to circumvent the development of rapid drug resistance.

SUMMARY OF THE INVENTION

It is therefore the objective of the present invention to provide a chemical compound that is able to bind to protozoan tubulin in order to prevent tubulin to polymerise into microtubules therefore inhibiting the protozoan replication in host cells.

This objective is achieved according to the present invention by the use of the compound parabulin and/or its derivates in the process of targeting protozoan tubulin for the inhibition of the replication of protozoans in human cells, wherein parabulin has the following structure and sum formula:

MW: 373.4 Da;

Formula: $C_{20}H_{23}N6_{O}$;

Name (s): 3-(3,4-dimethoxyphenyl)-N-[(3,4,5-trimethoxyphenyl)methyl]prop-2-enamide; (2E)-3-(3,4-Dimethoxyphenyl)-N-(3,4,5-trimethoxyphenyl)acrylamid;

SMILES:

O(C1=C(OC)C=CC(=C1)C=CC(=O)N(CC2=CC(=C(OC)C(=C2)OC)OC)[H])C.

Parabulin and/or its derivates are able to bind directly to protozoan tubulin. The addition of parabulin in an in vitro assay measuring the capability of mammalian tubulin to polymerise into microtubules led to a striking reduced numbers of growth events compared to the DMSO and colchicine controls.

Preferred embodiments of the present invention are hereinafter described in more detail with reference to the attached drawings which depicts in:

BRIEF DESCRIPTION OF THE FIGURES

FIG. 1 Protozoan and human tubulin and microtubule structures;

FIG. 4A is a graph depicting a toxicity assay showing the effect of parabulin and CA4 on cultured human fibroblast cells;

FIG. 4B is a graph showing the effect of parabulin on the replication rate of *Toxoplasma gondii*; and FIG. 4C is a graph showing a *Toxoplasma gondii* plaque assay for calculating the value of parabulin.

DETAILED DESCRIPTION OF THE INVENTION

Infectious diseases caused by apicomplexan parasites remain a global public health threat. The presence of multiple ligand-binding sites on tubulin makes it an attractive candidate for anti-parasite drug discovery. However, despite remarkable successes as anti-cancer agents, the rational development of parasite-specific tubulin drugs has been hindered by a lack of structural and biochemical information on protozoan tubulins. Here, atomic structures for a protozoan and human tubulin are presented, and the architectures of apicomplexan tubulin-drug binding sites is delineated. Based on this information, the parasite-specific tubulin inhibitor parabulin is disclosed for use while it is shown that its use inhibits the growth of parasites while displaying no effects on human cells. The present invention provides a framework to exploit structural differences between human and protozoa tubulin variants to enable the rational development of much-needed, novel parasite inhibitors.

Since the tubulin in parasites plays a major role in the replication of the parasite in the host, the present invention focusses on the possibilities to successfully disturb the process of the MT dynamics. Knowing that MTs are dynamic protein filaments made up of polymerized αβ-tubulin heterodimers the major disturbing impact on the phases of growth and shrinkage of the microtubules during the parasite replication can be effected by binding suitable agents to the tubulin thereby disturbing its capabilities on growth and/or shrinkage.

Attempts to produce recombinant apicomplexan tubulin for this purpose, proofed to be difficult. Therefore, it was decided to isolate tubulin dimers from a protozoa organism. Presently, the free-living ciliate *Tetrahymena thermophila* was chosen as its tubulin is abundantly expressed and nearly identical to apicomplexan tubulin. Ciliates and apicomplexans are phyla belonging to the alveolata group, and so do have relatively recent eukaryotic shared ancestry. Furthermore, apicomplexan tubulin inhibitors show similar activities on *T. thermophila*, suggesting that *T. thermophila* tubulin can be used as a close proxy to study the interaction of ligands to apicomplexan tubulin.

Figures 1A, 1B, 1C, 1D, 1E, 1F:
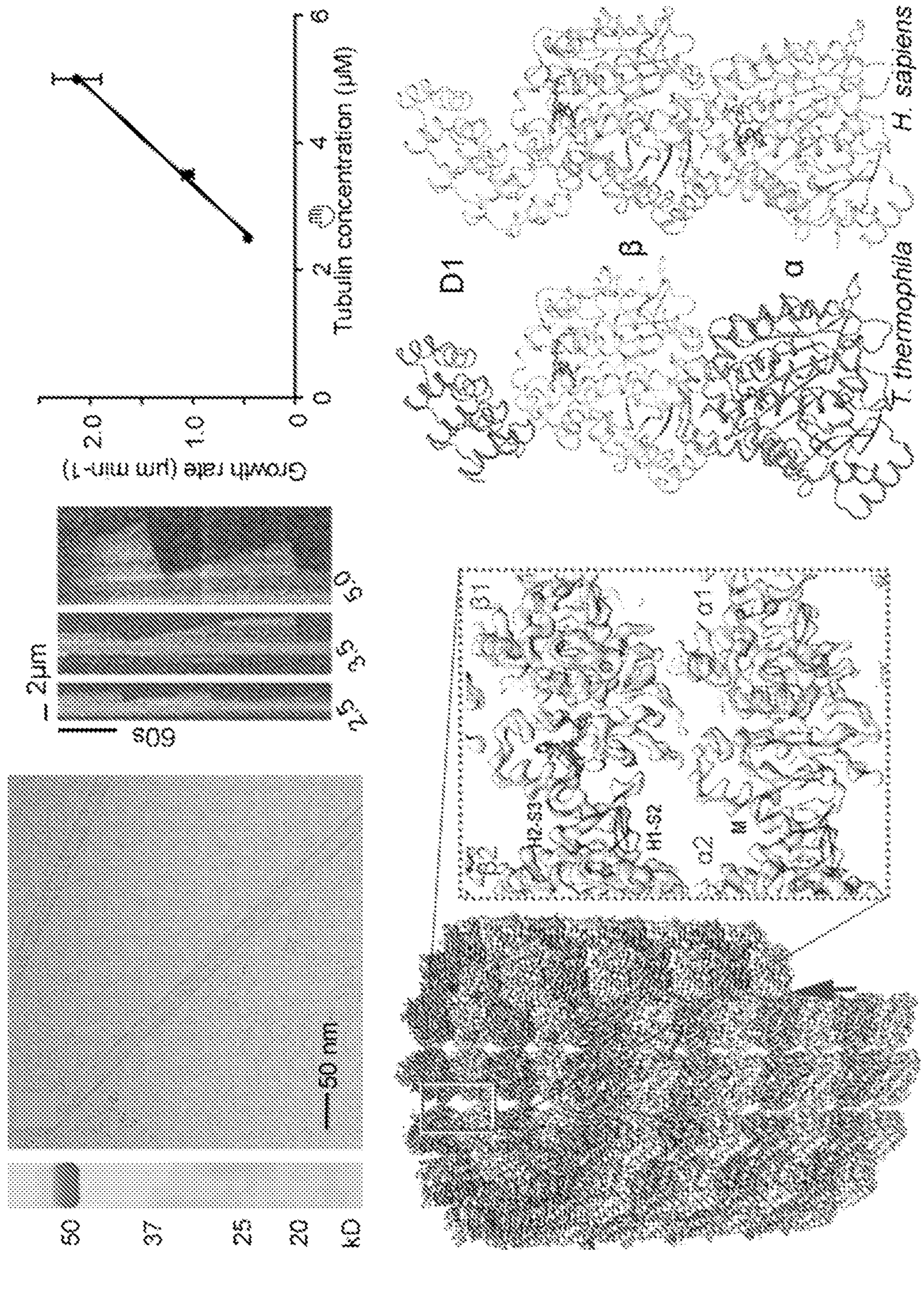
FIG. 1A is an illustration of a Coomassie stained SDS-PAGE.
FIG. 1B is an illustration showing a representative cryo-electron micrograph of paclitaxel-stabilized T.
FIG. 1C is an illustration showing kymographs of the dynamics of Tt-MTs.
FIG. 1D is a graph showing plots of Tt-MTs plus-end growth rates as a function of tubulin concentration.
FIG. 1E is an illustration showing cryo-electron microscopy density map of a 14 protofilament.
FIG. 1F is a cartoon representation of the crystal structures of Tt-tubuline-D1 and recombinant Hs-tubuline-D1 complexes.

FIG. 1 shows in (A) Coomassie stained SDS-PAGE showing purified *T. thermophila* tubulin. FIG. 1(B) shows a representative cryo-electron micrograph of paclitaxel-stabilized *T. thermophila* microtubules (Tt-MTs), while FIG. 1(C) depicts kymographs obtained by TIRF microscopy showing the dynamics of Tt-MTs at the indicated concentrations in μM. FIG. 1(D) is a plot of Tt-MT plus-end growth rates as a function of tubulin concentration. Error bars represent the mean +/−95% CI. FIG. 1(E) shows cryo-electron microscopy density map of a 14 protofilament, GMPCPP-stabilized Tt-MT with pseudohelical symmetry applied. Left: outside view. The α- and β-tubulin monomers are shown in ribbon representation and colored in dark and light gray, respectively. Red arrow shows the location of the seam. Right: tubulin dimer models fitted into a sliced, transparent and zoomed-in view. The paclitaxel structure in stick representation is highlighted in magenta. Lateral contacts between protofilaments are indicated in blue (H2-S3 in α2 and β2), red (H1-S2 in α2 and β2) and green (M loop in α1 and β1). FIG. 1(F) shows a cartoon representation of the crystal structures of Tt-tubulin-D1 (left) and recombinant Hs-tubulin-D1 (right) complexes.

Bound nucleotides are displayed in stick representation, the α- and β-tubulin monomers in dark and light gray ribbons, respectively.

*T. thermophila* tubulin was purified to homogeneity as described before (FIG. 1A). As shown in FIG. 1B, the purified protein readily polymerized into MTs in vitro as revealed by cryo-electron microscopy.

To obtain high resolution structural information on the *T. thermophila* tubulin, X-ray crystallography was used. To this end, subtilisin-treated *T. thermophila* αβtubulin in complex with Darpin1 (D1) was crystallized and the structure of the complex at 2 Å resolution was solved (FIG. 1F). To assess the structural differences between protozoan and their host mammalian tubulin, the structure of recombinant human α1β3-tubulin in complex with D1 was also crystallized and solved at 1.9 Å resolution (FIG. 1F).

Figures 2A, 2B, 2C, 2D:
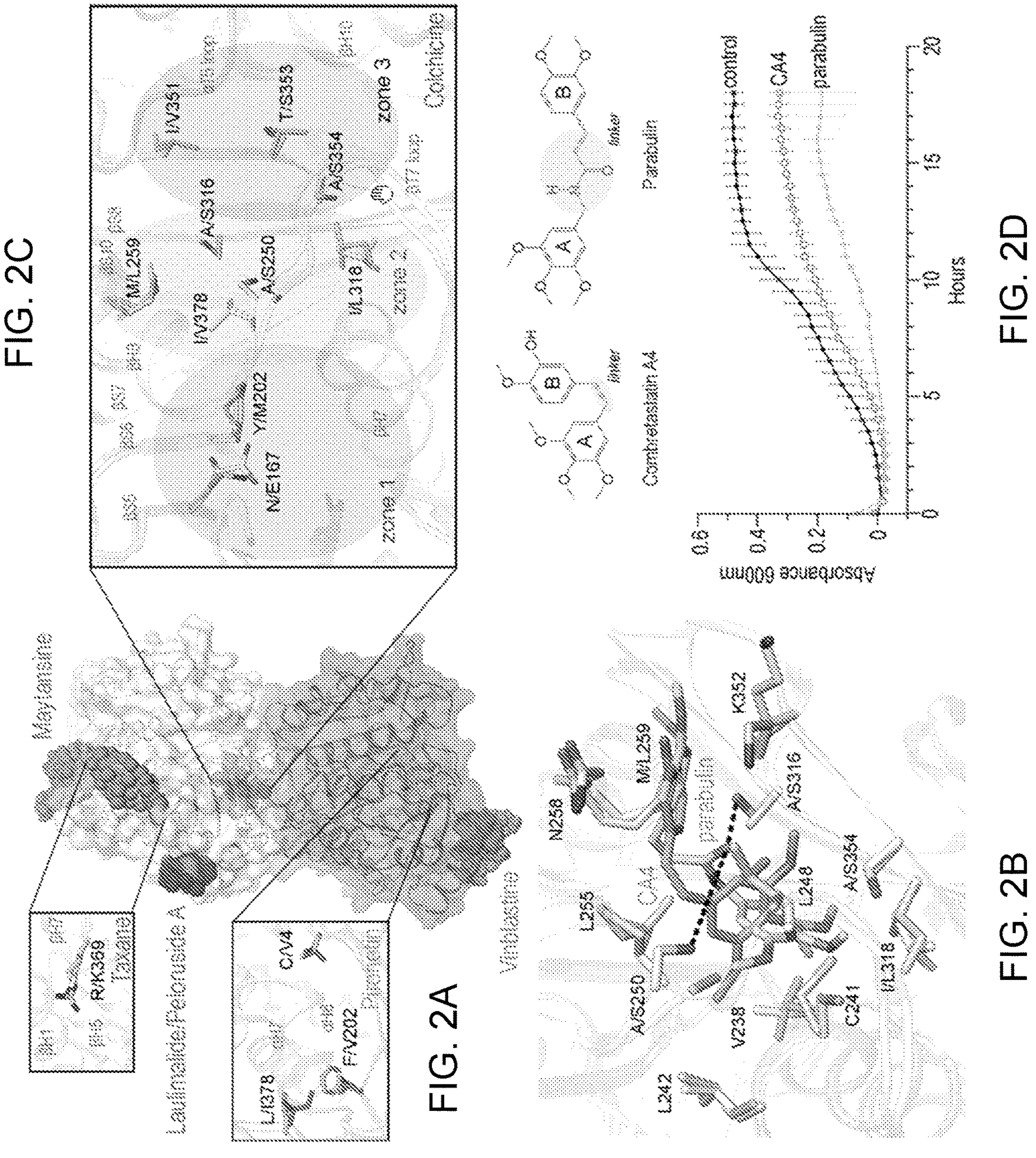
FIG. 2A is an illustration showing the Tt-tubulin structure.
FIG. 2B is an illustration showing a zoom out of the Colchicine site of the Tt-tubulin.
FIG. 2C is an illustration showing the chemical structure of CA4 and parabulin.
FIG. 2D is a graph plotting the time course of T.

The overall structure of *T. thermophila* tubulin is very similar to the human (rmsd of 0.49 over 751 Cα atoms) or the yeast ones (rmsd of 0.73 over 755 Cα atoms). One analysed and compared in detail all known drug-binding sites in human and *T. thermophila* tubulin to identify structural peculiarities of protozoan tubulin (FIG. 2A). The most prominent differences were observed in the colchicine site that is located at the alpha- and beta-tubulin intradimer interface. It is formed by residues of helices H7 and H8, the T7 loop, and the S8 and S9 strands of β-tubulin and is completed by the T5 loop of α-tubulin (FIG. 2A).

FIG. 2(A) shows the Tt-tubulin structure highlighting the six distinct drug binding sites found in mammalian tubulin. Zoom outs showing differences in the Taxane-, Pironetin— and Colchicine-sites between *T. thermophila* (light grey) and *H. sapiens* (wheat) tubulin. The three distinct zones of the Colchicine site are highlighted by colored transparent ovals. Amino acid residue differences between human and protozoa tubulin are indicated. Residues are displayed in stick representation and color coded accordingly to elements (N, blue; O, red; S, yellow; C, xxx for human and protozoa, respectively). FIG. 2(B) depicts a zoom out of the Colchicine site of Tt-tubulin showing the atomic arrangement of modelled CA4 (green) and parabulin (yellow). FIG. 2(C) represents the chemical structures of CA4 and parabulin. The two CA4 rings, denoted A and B, are highlighted as well as the linker (yellow). FIG. 2(D) is a plot showing the time course of *T. thermophila* cell growth in the presence of CA4 (20 μM) or parabulin (50 μM; error bars corresponding to the standard deviation of triplicate measurements).

It is known that Tubulin undergoes conformational change from a "curved" structure to a "straight" upon incorporation into MTs, which involves movements of strands S8 and S9 and a translation of helix H7 in both tubulin monomers, leading to a compaction of the colchicine site. Ligands binding to the colchicine site of tubulin thus "freeze" tubulin in the MT incompatible, curved conformation. Most notably, Ala250 and Ala316 of β-tubulin are changed to Ser250 and Ser316 in *T. thermophila* tubulin; notably, both serines are conserved among Apicomplexan parasites (FIGS. 2A and B).

To assess the activity of any putative anti parasitic compound, a turbidity based *T. thermophila* cell growth inhibition assay was put in place in parallel to the efforts to solve *T. thermophila* MT and tubulin structures.

As illustrated in FIG. 2C, compounds were found that showed activities in a range from no inhibition to partial inhibition of *T. thermophila* cell growth. Based on these results, Combretastatin A4 (CA4), a well-known anti-cancer agent currently in multiple clinical trials, was selected as a starting point for rational drug design with the aim to transform it into a parasite specific variant.

Based on structural modelling, it was anticipated that the two key changes in the colchicine site of *T. thermophila* tubulin (Ala250Ser and Ala316Ser) could offer an opportunity to modify CA4 for parasite specific binding (FIG. 2B). To this end, the aliphatic linker connecting the two aromatic rings in the CA4 molecule was modified to take advantage of the charge difference in the Colchicine site of *T. thermophila* tubulin (FIG. 2B). The molecules showing the most favourable interactions, were selected for the testing.

Among the various compounds only one compound was tested, which is dubbed parabulin, inhibited *T. thermophila* cell growth (FIG. 2C). To test if parabulin is able to bind to tubulin, its activity was assessed in vitro on dynamic MTs using our TIRF microscopy reconstitution assay. In contrast to the dynamic periods of growth and shrinkage observed for *T. thermophila* MTs (FIG. 1C), the addition of parabulin led to a striking reduction in the numbers of growth events (FIG. 3A).

Figure 3A:
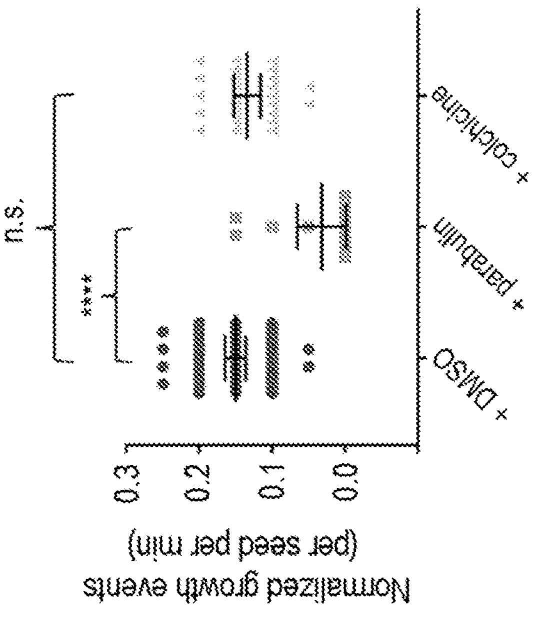
FIG. 3A is a graph showing the quantification of the Tt-MT growth events in TIRF microscopy MT dynamics reconstitution assays in the presence of the indicated drugs.
Figure 3B:
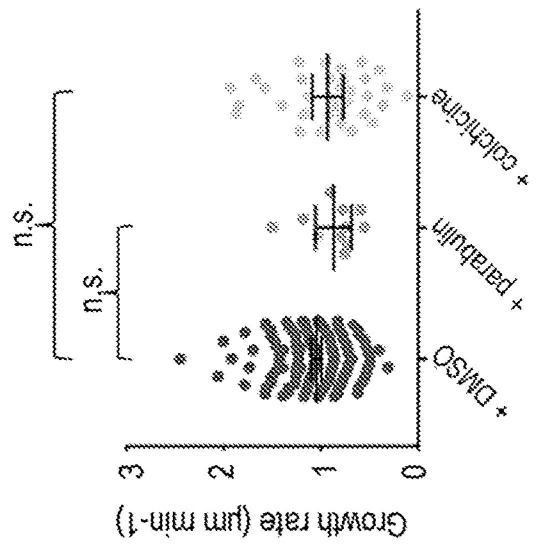
FIG. 3B is an illustration showing the Tt-MT growth rates in the presence of the indicated drugs.
Figure 3C:
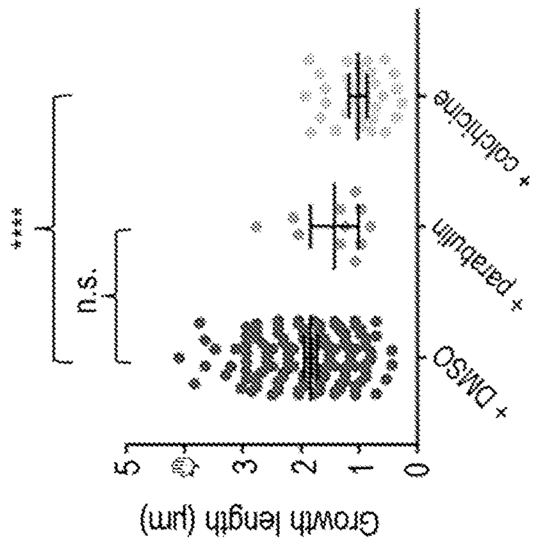
FIG. 3C is an illustration showing the Tt-MT length in the presence of the indicated drugs.

FIG. 3(A) is a plot showing the quantification of the Tt-MT growth events in TIRF microscopy MT dynamics reconstitution assays in the presence of the indicated drugs. Error bars represent the mean +/−95% CI. Rates were compared using one-way ANOVA with Tukey's multiple comparison test; DMSO vs parabulin P<0001 (****);

DMSO vs colchicine p=0.40 (n.s., not significant). FIG. 3(B) shows the Tt-MT growth rates in the presence of the indicated drugs (40 μM). Error bars represent the mean +/−95% CI. Rates were compared using one-way ANOVA with Tukey's multiple comparison test; DMSO vs parabulin P=0.25; DMSO vs colchicine P=0.20 (n.s., not significant). FIG. 3(C) represents the Tt-MT length in the presence of the indicated drugs (40 μM). Error bars represent the mean +/−95% CI. Rates were compared using one-way ANOVA with Tukey's multiple comparison test; DMSO vs parabulin P=0.15 (n.s., not significant); DMSO vs colchicine P<0001 (****).

The average number of growth events per 10-minute movie decreased from 41.3 to 3.8 even though the number of MT seeds immobilized on the cover slide was similar. When rare growth events occurred, no significant differences in growth rate (control vs parabulin P-value=0.25) or growth length (control vs parabulin P-value=0.15) were observed (FIG. 3BC). As a control, addition of colchicine did not lead to any significant changes in the dynamic properties of *T. thermophila* MTs (FIG. 3BC). Together with the present structural analyses, these results suggest that parabulin is a protozoan-specific MT-destabilizing agent.

To assess the potential of parabulin as a bona fide anti-parasitic agent, its effects were evaluated on cultures of human cells and growth of the apicomplexan parasite *Toxoplasma gondii* within human cells. When sub-confluent (proliferating) fibroblasts were exposed to parabulin or CA4 for 72 hours, parabulin exhibited considerably lower cytotoxicity than CA4 (99% cell survival at 25 μM against only 46% for CA4, FIG. 4A). CA4 has well-defined anti-mitotic activity due to its disruption of vertebrate MTs. In contrast, parabulin had little to no effect on fibroblasts growth, indicating that it does not disrupt vertebrate MTs or harbour other cytotoxic activity.

FIG. 4(A) depicts a toxicity assay showing the effect of parabulin and CA4 on cultured human fibroblast cells. FIG. 4(B) shows the effect of parabulin on the replication rate of *Toxoplasma gondii*. FIG. 4(C) shows a *Toxoplasma gondii* plaque assay for calculating the value of parabulin.

In order to assess the efficacy of parabulin, *T. gondii* tachyzoite replication was followed 36 h after addition of parabulin. A drastic reduction was observed in parasite replication compared to control cultures (no eight cell-stage observed compared to above 96% eight cell-stage for the controls, FIG. 4B). A *T. gondii* plaque assay was used to determine the concentration at which parasite replication is reduced by half ($EC_{50}$ value). When confluent fibroblast monolayers were infected with wild-type tachyzoites and left to grow for seven days, lytic parasite growth created visible holes in the vertebrate fibroblast monolayer. Both the plaque numbers and sizes were reduced by parabulin treatment. Quantification of the plaque area relative to control samples indicates that the parabulin has an $EC_{50}$ value of 6.5 μM (FIG. 4C). Taken together, these results validate the present drug design strategy and reveal that parabulin is a specific and potent inhibitor of protozoan MT functions.

Many of the current strategies to develop new therapeutic drugs to treat parasite infections focus on phenotypic screens to identify novel anti-parasitic agents. However, since parasites develop resistance quickly after introduction of new therapies, clever strategies are required to tackle deadly parasitic infections like malaria. Inhibiting essential parasite pathways using drug formulations targeting multiple sites on a single, essential parasite protein represents an attractive approach towards this end. Tubulin is a key component of the parasite cytoskeleton that is involved in multiple, essential parasite life processes including cell division, invasion and intracellular transport. Specific inhibition of parasite MTs by some drugs as well as exclusive parasite MT-based structures like the conoid, the apical complex and the sub-pellicular MTs highlight how much protozoan MTs are unique, structurally and biochemically, making them distinct from their human counterparts. These highly specialized apicomplexan MTs are essential parasite components making them excellent drug targets.

The present invention shows that it is possible to target specifically parasite tubulin without harming the human host cell. A compound has been identified that specifically alters parasite MTs and inhibits parasite replication and host cell invasion. The present disclosure thus illuminates a unique lead for the development of much-needed anti-parasitic agents and offers a basis to develop additional ligands binding to distinct and if required multiple sites of parasite tubulins.

The invention claimed is:

1. A method of inhibiting the replication of protozoans in a mammalian organism, comprising administering to the mammalian organism in need thereof a composition comprising parabulin, wherein the structure of parabulin is:

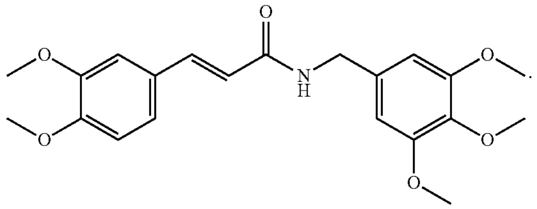

* * * * *